United States Patent

Ichioka et al.

[11] Patent Number: 5,847,256
[45] Date of Patent: Dec. 8, 1998

[54] PROCESS FOR PRODUCING XYLENE

[75] Inventors: Ryoji Ichioka; Shinobu Yamakawa, both of Nagoya; Hirohito Okino, Otsu, all of Japan

[73] Assignee: Toray Industries, Inc., Japan

[21] Appl. No.: 955,870

[22] Filed: Oct. 22, 1997

Related U.S. Application Data

[63] Continuation of Ser. No. 608,187, Feb. 28, 1996, abandoned.

[30] Foreign Application Priority Data

Mar. 6, 1995 [JP] Japan ..................................... 7-074587

[51] Int. Cl.$^6$ .................................................... C07C 15/08
[52] U.S. Cl. ......................... 585/470; 585/475; 585/486; 585/488; 585/489
[58] Field of Search ..................................... 585/470, 475, 585/483, 485, 489, 486, 488

[56] References Cited

U.S. PATENT DOCUMENTS

| | | | |
|---|---|---|---|
| 2,767,231 | 10/1956 | Kennedy et al. | 585/486 |
| 2,960,545 | 11/1960 | Seubold | 585/489 |
| 3,856,873 | 12/1974 | Burress | 585/486 |
| 4,236,996 | 12/1980 | Tabak et al. | 585/486 |
| 4,409,413 | 10/1983 | Iwayama et al. | 585/481 |
| 5,004,854 | 4/1991 | Yan | 585/489 |
| 5,516,956 | 5/1996 | Abichandani et al. | 585/486 |

FOREIGN PATENT DOCUMENTS

| | | | |
|---|---|---|---|
| 55-164631 | 12/1980 | Japan . | |
| 2052554 | 1/1981 | United Kingdom | 585/486 |

*Primary Examiner*—Wayne Langel
*Attorney, Agent, or Firm*—Austin R. Miller

[57] ABSTRACT

An improved process for producing xylene from feedstock containing $C_9$ alkyl aromatic hydrocarbons with the aid of a catalyst capable of disproportionation, rearrangement, and dealkylation, wherein said improvement comprises performing the reaction in the presence of an aromatic hydrocarbon having one or more ethyl groups in an amount of 5 to 50 wt %.

20 Claims, No Drawings

PROCESS FOR PRODUCING XYLENE

This application is a continuation of application Ser. No. 08/608,187, filed Feb. 28, 1996, abandoned.

BACKGROUND OF THE INVENTION

1. Field of the Invention

The present invention relates to a process for efficient production of xylene from feedstock containing $C_9$ alkyl aromatic hydrocarbons (which are generally regarded as useless) by disproportionation, transalkylation, and dealkylation, said process being carried out in the presence of a specific aromatic hydrocarbon whose concentration is within a certain range.

2. Description of the Prior Art

Xylene as a feedstock for p-xylene and o-xylene is usually produced from naphtha by reforming, followed by extraction and fractionation, or by extraction and fractionation of cracked gasoline as a by-product of thermal cracking of naphtha. Xylene is also produced on an industrial scale from toluene or a mixture of toluene and $C_9$ aromatic hydrocarbons by disproportionation and transalkylation of alkyl groups. However, toluene itself is an industrially important raw material for the production of benzene by dealkylation.

On the other hand, there has been disclosed in Japanese Patent Publication Nos. 48413/1974 and 16782/1975 a process for producing $C_{10}$ aromatic hydrocarbons (such as durene) from $C_9$ aromatic hydrocarbons (including propylbenzene isomers, methylethylbenzene isomers, and trimethylbenzene isomers) by disproportionation and transalkylation. However, nothing is known about the efficient production of xylene from feedstock composed mainly of $C_9$ aromatic hydrocarbons.

There is a known process for industrially producing xylene from toluene and $C_9$ aromatic hydrocarbons with the aid of amorphous silica-alumina catalyst. (PETROTECH, 2 (12) 1160, 1970) This process suffers the disadvantage that the catalyst has to be continuously regenerated by using a moving bed so as to maintain a certain level of yield and activity.

There has been reported a process for producing xylene from $C_9$ aromatic hydrocarbons alone or in combination with toluene with the aid of a zeolite catalyst. (J. Das et al., Catalysis Letter 23 (1994), I. Wang et al., Ind. Chem. Res. 29 (1990) 2005) This process is not necessarily satisfactory in yields.

So far, there has been no efficient process for producing xylene from $C_9$ aromatic hydrocarbons.

SUMMARY OF THE INVENTION

It is an object of the present invention to provide a process for efficiently producing xylene by disproportionation, transalkylation, and dealkylation from a feedstock composed mainly of substantially toluene-free $C_9$ aromatic hydrocarbons generally regarded as useless.

The present inventors found that it is possible to produce xylene efficiently from a feedstock composed mainly of substantially toluene-free $C_9$ aromatic hydrocarbons by disproportionation, transalkylation, and dealkylation if an aromatic hydrocarbon having one or more ethyl groups is present in a certain amount.

The gist of the present invention resides in an improved process for producing xylene from a feedstock containing $C_9$ alkyl aromatic hydrocarbons with the aid of a catalyst capable of disproportionation, transalkylation, and dealkylation, wherein said improvement comprises performing the reaction in the presence of an aromatic hydrocarbon having one or more ethyl groups in an amount of 5 to 50 wt %.

DETAILED DESCRIPTION OF THE INVENTION

The process of the present invention employs a feedstock composed mainly of $C_9$ alkyl aromatic hydrocarbons. It also employs an aromatic hydrocarbon having one or more ethyl groups, which is exemplified by ethylbenzene, methylethylbenzene, dimethylethylbenzene, and diethyl benzene.

According to the present invention, xylene is produced efficiently from a feedstock composed mainly of $C_9$ alkyl aromatic hydrocarbons with the aid of a catalyst capable of disproportionation, transalkylation, and dealkylation, in the presence of an aromatic hydrocarbon having one or more ethyl groups in an amount of 5 to 50 wt %, preferably 15 to 50 wt %.

The catalyst is not specifically restricted so long as it is capable of disproportionation, transalkylation, and dealkylation. It should preferably be one which contains zeolite. A preferred zeolite is mordenite.

The zeolite should contain at least one member selected from the metals belonging to the VIB, VIIB, and VIII Groups, in an amount of 0.001–5 wt %, preferably 0.02–1 wt % (as an element). A preferred example of the metal is rhenium.

The reaction involving the above-mentioned catalyst should be carried out in the presence of hydrogen at 1–6 MPa and 300°–550° C., with the WHSV (weight hourly space velocity) being 0.1–10/hr.

EXAMPLES

The invention will be described with reference to the following examples.

Example 1

A pasty mixture was prepared by mixing 105 g of powdery synthetic mordenite(sodium form), 45 g of α-alumina, 12 g of alumina sol (containing 10 wt % alumina), 10.5 g of alumina gel (containing 70 wt % alumina), and an adequate amount of deionized water. After kneading for about 2 hours, the pasty mixture was molded into cylindrical pellets, each measuring 1.0 mm long and 1.2 mm in diameter. The pellets were dried at 120° C. for 16 hours. The dried pellets (50 g in absolute dry condition at 520° C.) were baked at 400° C. for 5 hours in an atmosphere of air. After cooling, the baked pellets were treated with 100 g of 10 wt % aqueous solution of ammonium chloride at 80°–85° C. for 1 hour. The treated pellets were strained off the solution and thoroughly washed with water. The pellets were treated with 100 g of 5 wt % aqueous solution of tartaric acid at 80° to 85° C. for 3 hours. The treated pollets were strained off the solution and thoroughly washed with water. The washed pellets were dipped in 6.5 g of 5 wt % aqueous solution of rhenium(VII) oxide ($Re_2O_7$) at room temperature for impregnation with rhenium. The pellets were dried again at 120° C. for 16 hours and then baked at 540° C. for 8 hours in an atmosphere of air. Thus, there was obtained hydrogen ion exchanged mordenite catalyst (A). This catalyst (A) contained 0.25 wt % of rhenium (in absolute dry condition at 520° C.).

Using this catalyst (A) in a fixed-bed catalytic reactor, xylene was produced from a feedstock composed of trimethylbenzene (TMB for short) as a $C_9$ alkyl aromatic hydrocarbon and methylethylbenzene (ET for short) as an aromatic hydrocarbon having an ethyl group in varied ratios. The reaction conditions were as follows:

Temperature: 400° C.

Pressure: 4 MPa

WHSV: 2.5 h-1

H/2 feedstock: 4.0 mol/mol

The results are shown in Table 1. It is noted that the yield of xylene increases as the amount of ET increases up to 50 wt %. However, beyond this limit, the yield of xylene decreases.

TABLE 1

| Run No. | Ratio (by weight) of ET/(TMB + ET) in feedstock | Amount (g) of xylene produced per 100 g of feedstock |
|---|---|---|
| 1 | 0 | 20 |
| 2 | 0.25 | 31 |
| 3 | 0.45 | 34 |
| 4 | 0.65 | 28 |

Example 2

Using the catalyst (A) in a fixed-bed catalytic reactor, xylene was produced in the same manner as in Example 1 from a feedstock in which ET was replaced by ethylbenzene (EB for short) or diethylbenzene (DEB for short).

The results are shown in Table 2. It is noted that the yield of xylene is favorably affected by both EB and DEB.

TABLE 2

| Run No. | Composition (by weight) or feedstock | Amount (g) of Xylene produced per 100 g of feedstock |
|---|---|---|
| 1 | TMB + EB (EB/TMB = 30/70) | 34 |
| 2 | TMB + DEB (DEB/TMB = 35/65) | 34 |

Example 3

Catalysts were prepared in the same manner as in Example 1 except that the amount of rhenium was varied. Using the catalysts in a fixed-bed catalytic reactor, xylene was produced in the same manner as in Example 1 from the same feedstock as used in Run No. 3 in Example 1.

The results are shown in Table 3. It is noted that the yield of xylene increases with the increasing amount of rhenium in the range of 0.01 wt % to 0.02 wt %. The effect of rhenium levels off beyond 0.10 wt %.

TABLE 3

| Run No. | Content of rhenium as element (wt %) | Amount (g) of xylene produced per 100 g of feedstock |
|---|---|---|
| 1 | 0 | 20 |
| 2 | 0.01 | 23 |
| 3 | 0.02 | 32 |
| 4 | 0.10 | 34 |
| 5 | 0.20 | 34 |

Example 4

Six catalysts (B to G) were prepared, each containing rhenium, nickel, cobalt, molybdenum, chromium, or tungsten. The first four catalysts (B to E) were prepared in the same manner as in Example 1 by impregnation with an aqueous solution containing each metal element. The last two catalysts (F and G) were also prepared in the same manner as in Example 1 except that the compound shown in Table 4 was incorporated into the catalyst components at the time of mixing.

TABLE 4

| Catatyst | Metal | Compound | Incorporated by |
|---|---|---|---|
| B | Re | $Re_2O_7$ | Dipping and impregnation |
| C | Ni | $Ni(NO_3)_2 6H_2O$ | Dipping and impregnation |
| D | Co | $Co(NO_3)_2 6H_2O$ | Dipping and impregnation |
| E | Mo | $(NH_4)_6Mo_7O4H_2O$ | Dipping and impregnation |
| F | Cr | $CrO_3$ | Mixing |
| G | W | $WO_3$ | Mixing |

Using each catalyst (B to G) in a fixed-bed catalytic reactor, xylene was produced under the same condition as in Example 1 from the same feedstock as used in Run No. 3 in Example 1. The results are shown in Table 5. It is noted that the catalyst containing rhenium is most active with the minimal content.

TABLE 5

| Catalyst | Metal | Content (wt %) of metal (as element) in catalyst | Amount (g) of xylene produced from 100 g of feedstock |
|---|---|---|---|
| B | Re | 0.15 | 34 |
| C | Ni | 0.40 | 30 |
| D | Co | 0.40 | 26 |
| E | Mo | 0.40 | 32 |
| F | Cr | 0.40 | 28 |
| G | W | 0.24 | 22 |

Example 5

Three catalysts, each containing a different amount of rhenium, were prepared in the same manner as in Example 1. Using each catalyst in a fixed-bed catalytic reactor, xylene was produced under the same condition as in Example 1 from the same feedstock as used in Run No. 3 in Example 1. The rate of decrease in yield was recorded. The results are shown in Table 6. It is noted that the catalyst becomes less liable to deterioration in proportion to the amount of rhenium contained therein.

TABLE 6

| Content (wt %) of rhenium (as element) in catalyst | Decrease in yield of xylene (wt % per day) |
|---|---|
| 0 | 1.50 |
| 0.01 | 0.96 |
| 0.20 | less than 0.04 |

What is claimed is:

1. In an improved process for producing xylene in a reactor from a feedstock containing $C_9$ alkyl aromatic hydrocarbons with the aid of a catalyst capable of disproportionation, transalkylation, and dealkylation, the improvement comprising reacting said feedstock in the presence of an aromatic hydrocarbon having one or more ethyl groups in an amount of 15 to 50 wt %, based on the weight of all reactants in said reactor, and said catalyst.

2. The process for producing xylene as defined in claim 1, wherein the catalyst is one which contains a zeolite.

3. The process for producing xylene as defined in claim 2, wherein the zeolite is mordenite zeolite.

4. The process for producing xylene as defined in claim 3 wherein the zeolite is one which contains at least one metal selected from the group consisting of Group VIB metals, Group VIIB metals and Group VIII metals, in an amount of 0.001 to 5 wt %.

5. The process for producing xylene as defined in claim 2 wherein the zeolite is one which contains at least one metal selected from the group consisting of Group VIB metals, Group VIIB metals, and Group VIII metals, in an amount of 0.001 to 5 wt %.

6. The process for producing xylene as defined in claim 5, wherein the metal is rhenium.

7. The process for producing xylene as defined in claim 6, wherein the zeolite contains elemental rhenium in an amount of 0.02 to 1 wt %.

8. The process defined in claim 1, wherein said feedstock is substantially toluene free.

9. In an improved process for producing xylene in a reactor from a feedstock containing $C_9$ alkyl aromatic hydrocarbons with the aid of a catalyst capable of disproportionation, transalkylation, and dealkylation, the improvement comprising reacting said feedstock in the presence of an aromatic hydrocarbon having one or more ethyl groups in an amount of 15 to 50 wt %, based on the weight of all reactants in said reactor, at 1–6 MPa and 300°–550° C., in the presence of hydrogen and said catalyst, with the WHSV being 0.1–10/hr.

10. The process for producing xylene as defined in claim 9, wherein the catalyst is one which contains a zeolite.

11. The process for producing xylene as defined in claim 10, wherein the zeolite is mordenite zeolite.

12. The process for producing xylene as defined in claim 11 wherein the zeolite is one which contains at least one metal selected from the group consisting of Group VIB metals, Group VIIB metals and Group VIII metals, in an amount of 0.001 to 5 wt %.

13. The process for producing xylene as defined in claim 12, wherein the metal is rhenium.

14. The process for producing xylene as defined in claim 13, wherein the zeolite contains elemental rhenium in an amount of 0.02 to 1 wt %.

15. The process for producing xylene as defined in claim 10 wherein the zeolite is one which contains at least one metal selected from the group consisting of Group VIB metals, Group VIIB metals and Group VIII metals, in an amount of 0.001 to 5 wt %.

16. The process defined in claim 9, wherein said feedstock is substantially toluene free.

17. A process for producing xylene comprising:
    supplying a substantially toluene free feedstock containing $C_9$ alkyl aromatic hydrocarbons to a reaction chamber;
    providing a zeolite catalyst in said reaction chamber;
    supplying an aromatic hydrocarbon having one or more ethyl groups in an amount of 15 to 50 wt %, based on the weight of all reactants in said reaction chamber, to said reaction chamber; and
    reacting said feedstock in said reaction chamber so as to produce xylene.

18. The process defined in claim 17 wherein said at least one metal is rhenium.

19. The process defined in claim 17 further comprising supplying hydrogen into said reaction chamber at WHSV of 0.1–10/hr.

20. The process defined in claim 17 wherein xylene is produced at a rate of 22–34 gms/100 gms of said feedstock.

* * * * *